United States Patent [19]

Seelye et al.

[11] Patent Number: 4,730,062
[45] Date of Patent: Mar. 8, 1988

[54] PROCESS OF PREPARATION OF TETRAFLUORO 2,3-DIHYDROBENZOFURANS

[75] Inventors: David E. Seelye, Newtown; Ernest L. Plummer, Yardley, both of Pa.

[73] Assignee: FMC Corporation, Philadelphia, Pa.

[21] Appl. No.: 725,193

[22] Filed: Apr. 19, 1985

[51] Int. Cl.$^4$ ........................................... C07D 307/82
[52] U.S. Cl. .................................... 549/462; 548/454; 549/470
[58] Field of Search ................. 549/462, 470; 548/454

[56] References Cited

U.S. PATENT DOCUMENTS 4,377,711 3/1983 Rico et al. ........................... 568/656

FOREIGN PATENT DOCUMENTS 15577 9/1980 European Pat. Off. .
1416181 12/1975 United Kingdom .
1420211 1/1976 United Kingdom .

OTHER PUBLICATIONS

Bradsher et al., J. Org. Chem., vol. 46, pp. 1384–1388, (1981).
Fieser et al. I, Adv. Org. Chem., Reinhold, pp. 113 & 114, 649 & 785, (1961).
Fieser et al. II, Reagents for Org. Synthesis, vol. 1, pp. 157 & 158, (1967).
Fieser et al. III, Reagents for Org. Synthesis, vol. 9, p. 122, (1981).
Bailey et al., Tet. Letters, No. 11, pp. 869–870, (1975).
Malyuta et al., Tetrahedron, 31(9), pp. 1201–1207, (1975).
Maksimov et al., J. of Fluorine Chem., p. 166, (Aug. 1985).
Lothrop, J.A.C.S., 63, pp. 1187–1191.
Fuson, Organic Synthesis, Collective vol. III, pp. 339–340, (1960).
Salfeld et al., Tet. Letters, No. 28, pp. 3365–3367, (1966).
Fanta, Chem. Reviews, 64, pp. 613–632, (1964).
March, Advanced Org. Chem., 3rd Ed., Wiley, pp. 597–598, (1985).

Primary Examiner—Richard A. Schwartz
Assistant Examiner—Bernard I. Dentz
Attorney, Agent, or Firm—Patrick C. Baker; H. Robinson Ertelt

[57] ABSTRACT

Tetrafluorobenzofurans of the formula

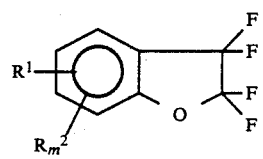

are prepared by contacting, at elevated temperature in an aprotic solvent, an ether of the formula

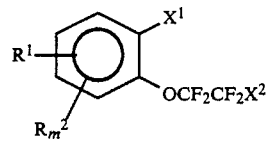

with a catalytic mixture of metallic cooper and a polydentate or other ligand, wherein $R^1$ is hydrogen, nitro, amino, phthalimido or acetylimido, $R^2$ is at least one of hydrogen, halo, cyano, alkyl, hydroxy, alkoxy, acyl, acyloxy, alkoxycarbonyl, alkoxycarbonylalkyl, phenyl, phenyloxy, trifluoromethyl or dialkylamino. The products are intermediates in the preparation of pyrazoline insecticides.

11 Claims, No Drawings

PROCESS OF PREPARATION OF TETRAFLUORO 2,3-DIHYDROBENZOFURANS

RELATED APPLICATION

This application is related to application Ser. No. 664,674, filed Oct. 25, 1984, of A. J. Duggan entitled "Pyrazoline Insecticides" and a continuation-in-part application thereof, Ser. No. 709,626 filed Mar. 8, 1985.

BACKGROUND OF THE INVENTION

This invention relates to fluorine-substituted benzofurans, and more particularly to tetrafluoro benzofurans, their synthesis, and use of the tetrafluoro benzofurans as intermediates for the preparation of certain pyrazoline insecticides described in the applications referred to above.

The furanyl ring cannot be selectively fluorinated in an effective manner, particularly when substituted other than by fluorine. It is necessary, therefore, to develop, and it is an object of the present invention to provide, a method of indirectly incorporating fluorine into the furanyl ring in order to provide intermediates for synthesis of the aforementioned pyrazoline insecticides. The latter synthesis is summarized hereinafter.

The coupling of halogenated aromatic and aliphatic compounds to form fluoroalkyl-substituted aromatic compounds is known (British Pat. Nos. 1416181 and 1420211). However, the coupling does not involve ring closure of a fluorinated ether group on an aromatic nucleus to form a fluorinated benzofuran as in the present invention. 2,2,3,3-Tetrafluorobenzofuran is known (Tetrahedron Letters, No. 11, 869-870, 1975) but not when carrying other substituents.

SUMMARY OF THE INVENTION

The tetrafluoro benzofurans of the present invention have the formula (I):

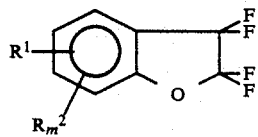

wherein $R^1$ is hydrogen, nitro, amino, phthalimido or acetamido, $R^2$ is hydrogen or a substituent which is non-interfering in the cyclization reaction leading to the formation of the compounds, as described below, m is 0–3, and at least one of $R^1$ and $R^2$ is other than hydrogen. Typically, $R^2$ is halo, cyano, alkyl, hydroxy, alkoxy, acyl, acyloxy, alkoxycarbonyl, alkoxycarbonylalkyl, phenyl, phenyloxy, trifluoromethyl or dialkylamino. The benzofurans of formula I, further including benzofurans wherein both $R^1$ and $R^2$ are hydrogen, are prepared by a cyclization reaction in which an ether of the formula (II):

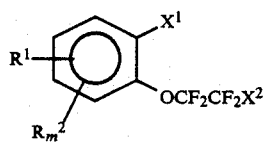

is contacted, at elevated temperature in an aprotic solvent medium, with a catalytic mixture of metallic copper and a polydentate or other ligand. In formula II, $R^1$, $R^2$ and m are the same as in formula I (except that both $R^1$ and $R^2$ may be hydrogen), and $X^1$ and $X^2$ independently are chloro, bromo or iodo.

DETAILED DESCRIPTION

In formula I, halo includes fluoro, chloro, bromo and iodo. Alkyl (which includes cycloalkyl and the alkyl groups in dialkylamino) and alkoxy preferably are lower alkyl or lower alkoxy, respectively, i.e., straight or branched chains containing 1–8 carbon atoms. Preferably, the acyl, acyloxy, alkoxycarbonyl and alkoxycarbonylalkyl groups also contain 1–8 carbon atoms in each of the hydrocarbon portions of these groups. Typical $R^2$ groups therefore are methyl, ethyl, propyl, butyl, pentyl, hexyl, cyclohexyl, heptyl, octyl, methoxy, ethoxy, butoxy, acetyl, acetoxy, methoxycarbonyl, methoxycarbonylmethyl, dimethylamino, diethylamino, and the like, including isomers. When m is 2 or 3, the $R^2$ groups may be the same or different.

The tetrafluoro benzofurans are conveniently prepared by heating a tetrafluoro ether of formula II with a mixture of metallic copper and a polydentate or other ligand in an aprotic solvent. Tetrafluoro ethers of formula II can be readily prepared by reactions analogous to those described in U.S. Pat. No. 4,377,711 to Rico et al. issued Mar. 22, 1983. For example, ethers within the scope of the patent and having a chloro, bromo or iodo group ortho to a bromotetrafluoro ethoxy group may be prepared by reacting 1,2-dibromotetrafluoroethane with potassium 2-chloro-4-nitrophenolate in an anhydrous polar, aprotic solvent medium.

Suitable reaction solvents for cyclization of the ethers II to benzofurans I are aprotic organic solvents, preferably polar, such as dimethylformamide, dimethyl sulfoxide, hexamethylphosphorous triamide, dimethylacetamide, N-methylpyrrolidone and sulfolane, including any mixtures thereof. The solvent is used in an amount effective to dissolve or disperse the reactive components and to provide a fluid medium. Preferably, the reaction is run under anhydrous conditions.

Reaction temperature should be higher than the melting point of ether II and typically will be in the range of about 50° C. to 150° C. at atmospheric or autogenous pressure, preferably about 100° C.–140° C. Other temperatures may be used depending on the solvent, the ether reactant and reaction pressure. For example, if the solvent is dimethyl sulfoxide and $R^1$ of ether II is nitro, an effective temperature which also avoids decomposition of the solvent is about 130°–140° C. and reaction time is about 10 minutes. For the same solvent but with an ether II wherein $R^1$ is acetamido, an effective reaction temperature is about 110° C. for a reaction time of about 5 hours. The reaction may be run at reflux in some cases, again depending on the solvent and the ether undergoing cyclization. Subatmospheric or superatmospheric pressures may also be used, with appropriate temperature adjustment.

The catalytic mixture or complex of copper metal and ligand may be preformed or formed in situ in the reaction medium. The copper preferably is used in finely divided form, such as a powder, and more preferably as an activated form thereof prepared by treating copper powder in acetone with anhydrous iodine as described in Organic Synthesis, III, 399.

Suitable ligands include bidentate, tridentate ligands and others which form stable copper complexes, such as 2,2'-di-pyridyl, 1,10-phenanthroline and substituted derivatives thereof, for example, 5,5'-diethyl-2,2'-dipyridyl, 4,4'-dimethyl-2,2'-dipyridyl, 4,4'-diphenyl-2,2'-dipyridyl, 4,4'-di(ethoxycarbonyl)-2,2'-dipyridyl, 2,9-dimethyl-4,7-diphenyl-1,10-phenanthroline, and 2,9-dimethyl-1,10-phenanthroline. Other ligands include 2,2'-diquinolyl, di(2-pyridyl)methane, 3-hydroxyquinoline, thiourea, rubeanic acid (dithio oxamide), 2,2',2''-terpyridine and 1,1,1-tris(dimethylphosphinomethyl)ethane.

The metallic copper is preferably used in large excess with respect to the ether II, of the order of about 2-4 moles of copper per mole of ether. The ligand may be used in the range of about 1/30 mole to about 10 moles per mole of ether. Generally, the amounts of copper and ligand may be varied as required to accommodate other conditions of the cyclization reaction, including the particular ether undergoing reaction, the solvent system, and reaction temperature and pressure.

The metallic copper-ligand complexes of the type found effective in the present invention are described in British patents 1416181 and 1420211 for use in catalyzing the coupling of halogenated aromatic and aliphatic compounds to form fluoroalkyl-substituted aromatic compounds. The specifications of these patents are incorporated herein by reference.

The benzofuran reaction product (I) is a solid which may be separated from the reaction mixture by any of the many suitable means known in organic synthesis, such as chromatographic separation or filtration combined with solvent stripping.

$R^1$ and/or $R^2$ substituents other than hydrogen may also be attached by known methods of a tetrafluorobenzofuran nucleus I after cyclization of an ether II which lacks the substituent. For example, cyano may be introduced by reacting compound I where $R^1$ is hydrogen and $R^2$ is halo with CuCN in pyridine (Rosenmund-Von Braun reaction). The cyano group thereby replaces the halo group. Similarly, cyano initially can be attached as an $R^1$ substituent to a tetrafluorobenzofuran nucleus I by cyclization of an ether II wherein $R^1$ is halo followed by substitution of the halogen with cyano. The cyano may then be converted in two steps to amino in a known manner as described below.

The tetrafluoro benzofuran reaction products (formula I) are readily converted to pyrazoline insecticides by substitution of $R^1$ with an isocyanate or thioisocyanate group, and then coupling the resulting product with an appropriately substituted pyrazoline, as described in the related U.S. applications cited above. If $R^1$ is nitro, reduction to amino (—$NH_2$) is effected before the isocyanate or thiocyanate substitution. Conventional reducing agents and conditions may be employed for this purpose, such as hydrogenation in methanol with a platinum catalyst. If $R^1$ is phthalimido or acetamido, reduction to amino is effected by reaction with hydrazine. If $R^1$ and $R^2$ are hydrogen or if $R^1$ is hydrogen and $R^2$ is halo or alkyl, the benzofuran nucleus may be nitrated ($R^1$=$NO_2$) by conventional techniques (for example, by treatment with a cold mixture of nitric and sulfuric acids) to provide products suitable for conversion to pyrazolines in the manner described below, it being understood that the nitro group will be reduced to amino before the conversion to pyrazoline. If $R^1$ and/or $R^2$ is cyano, the cyano group may be converted to carboxyl by reaction with sodium hydroxide and ethylene glycol, and then to amino by a Schmidt amination (reaction with sodium azide and sulfuric acid), in a known manner.

In brief outline, the pyrazoline synthesis typically proceeds as follows, with further details to be found in the copending applications (incorporated herein by reference) and in the examples hereinafter set forth:

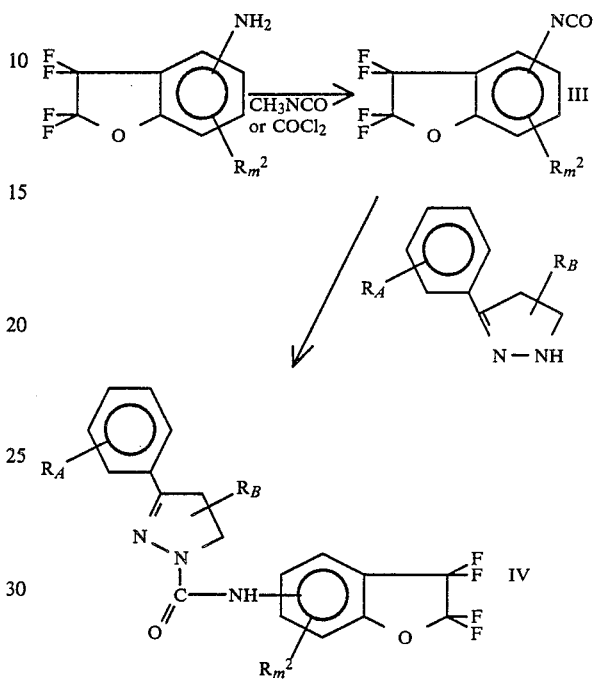

In the above reaction, $R^2$ is the same as defined in formulas I and II hereinabove, $R_A$ is hydrogen, halogen, haloalkyl or haloalkoxy, and $R_B$ is a 4- or 5-substituent of the formula

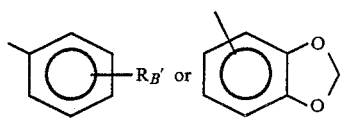

wherein $R'_B$ is hydrogen, halogen or haloalkyl. In formula IV, the amino group linking the tetrafluoro benzofuran and pyrazoline nuclei may be alkylated in a known manner whereby the hydrogen is replaced with alkyl to define the substituent $R_N$ of the generic pyrazoline formula of the copending applications identified above.

Pyrazolines of formula IV exhibit good insecticidal activity against southern armyworm (*Spodoptera eridania*) and Mexican bean beetle (*Epilachna varivestis*). For example, against the southern armyworm a pyrazoline of formula IV wherein $R_A$ is —$OCHF_2$, $R_B$ is 4-phenyl and $R^2$ is hydrogen (m=0) exhibited 100% mortality at a concentration of 8 ppm. Against the Mexican bean beetle, 100% mortality at 8 ppm concentration was achieved by application of the same pyrazoline.

The pyrazolines of formula IV are employed as insecticides in the conventional manner. Accordingly, they may be applied neat but more usually are formulated as blends with agriculturally acceptable carriers and surfactants and applied as sprays, dusts or granules to the locus where pest control is desired. Type of formulation and concentration of pyrazoline will vary according to the pest and the environment. Thus, the pyrazolines may be formulated as granules of large particle size, as powdery dusts, as wettable powders, as emulsifiable concentrates, as solutions, or in other form. When a formulation is diluted for application, the pyrazoline will normally be present in the range of about 0.001% to about 10% by weight. The locus of application may be the insects themselves, plants upon which the insects feed, or the insect habitat, including soil in which plants are or are about to be planted.

Additional details of the insecticidal utility and modes of insecticidal application are set forth in the copending Duggan applications identified above, and the skilled formulator is fully aware and capable of formulating and applying the pyrazolines for insect control in a wide variety of environments, based on the extensive literature on the subject as represented by U.S. Pat. No. 4,174,393, for example.

The following examples will serve as further illustration of the invention but are not intended necessarily as limitations on the scope thereof. In the examples and elsewhere in this specification, all parts and percentages are by weight, all temperatures are °C., and all pressures are mm Hg, unless otherwise stated.

EXAMPLE 1

Preparation of 2,2,3,3-tetrafluoro-5-nitrobenzofuran (A) Into a pressure bottle was placed 15.0 g (0.086 mole) 2-chloro-4-nitrophenol, 11.9 g (0.086 mole) potassium carbonate, 1.5 g (0.02 mole) propanethiol, 33.7 g (0.13 mole) 1,2-dibromotetrafluoroethane and 115 ml of N,N-dimethylformamide. The pressure bottle was sealed and the mixture stirred at 50° C. for 48 hours. The pressure bottle was cooled to room temperature, opened, and the contents poured into a separatory funnel. Approximately 200 ml of a 2N sodium hydroxide solution was added to the separatory funnel. The resultant mixture was extracted with four 300 ml portions of diethyl ether. The extracts were combined and washed with two 100 ml portions of a 2N sodium hydroxide solution. The washed extract was dried over anhydrous magnesium sulfate and filtered. The filtrate was evaporated under reduced pressure leaving an oil. The reaction described above was repeated three additional times. The residual oils from the four runs were combined and purified by column chromatography on silica gel, eluting with n-heptane: toluene (95:5), to yield 57.6 g of 3-chloro-4-(2-bromo-1,1,2,2-tetrafluoroethoxy)nitrobenzene as an oil.

(B) Into a pressure bottle was placed 10.0 g (0.028 mole) of the 3-chloro-4-(2-bromo-1,1,2,2-tetrafluoroethoxy)nitrobenzene prepared in (A) above, 9.0 g (0.14 mole) copper powder (200 mesh), 0.45 g (0.0028 mole) 2,2'-bipyridyl, and 40 ml of dimethyl sulfoxide (DMSO). The pressure bottle was sealed and the reaction mixture stirred at 190°–195° C. for two hours. The pressure bottle was cooled to room temperature, opened, and the contents poured into a separatory funnel. Approximately 200 ml of a 2N hydrochloric acid solution was added to the separatory funnel. The mixture was extracted with three 150 ml portions of diethyl ether. The extracts were combined and washed in succession with 200 ml of a 2N hydrochloric acid solution, 200 ml of a saturated aqueous sodium chloride solution, and 200 ml of a 2N sodium hydroxide solution. The washed extract was dried over anhydrous magnesium sulfate and filtered. The solvent was evaporated under reduced pressure leaving an oil. The reaction described above was repeated six additional times. The residual oils from the seven runs were combined and subjected to column chromatography on silica gel, eluting with toluene, to yield a yellow oil. This oil was dissolved in 125 ml of methylcyclohexane and the solution placed in a freezer for approximately 18 hours. Crystals formed and were collected by filtration to yield 20.7 g 2,2,3,3-tetrafluoro-5-nitrobenzofuran. The filtrate was evaporated under reduced pressure leaving an oil. Distillation of this oil under reduced pressure provided an additional 3.0 g of product (bp 75° C./0.2 mm Hg).

EXAMPLES 2–16

Essentially as described in Example 1 (except for the compounds of Examples 12–16) and as depicted in the following reaction, other tetrafluoro benzofurans were prepared from the corresponding tetrafluoro ethers. The compounds of Examples 12, 13, 15 and 16 were prepared by reduction of the corresponding tetrafluoronitrobenzofurans of Examples 10, 1, 2 and 3 using the hydrogenation procedure described in Example 17, Part A. The compound of Example 14 was prepared by reaction of the compound of Example 5 with CuCN in pyridine (Rosenmund-Von Braun synthesis).

The resulting tetrafluoro benzofurans (including that of Example 1) are identified in Table I together with melting points (mp) and elemental analyses (C=carbon, H=hydrogen). In each synthesis the nmr spectrum of each product compound was consistent with the proposed structure.

TABLE I

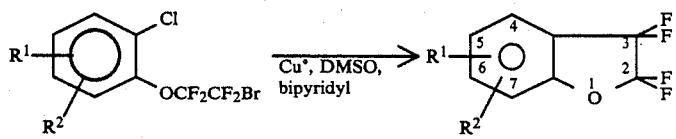

| Example | R¹ | R² | mp (°C.) | Elemental Analysis C | H |
|---|---|---|---|---|---|
| 1 | 5-NO₂ | H | 54–55 | Calc'd 40.52 | 1.27 |
|   |   |   |   | Found 40.51 | 1.08 |
| 2 | 6-NO₂ | H | 64–64.5 | Calc'd 40.52 | 1.27 |
|   |   |   |   | Found 39.42 | 1.30 |
| 3 | 7-NO₂ | H | 61–62 | Calc'd 40.52 | 1.27 |
|   |   |   |   | Found 39.82 | 1.28 |
| 4 | H | 4-Cl | oil |   |   |
| 5 | H | 5-Cl | oil | Calc'd 42.41 | 1.33 |

TABLE I-continued

R¹—[benzene ring with Cl and OCF₂CF₂Br substituents, R² on ring] —Cu°, DMSO, bipyridyl→ R¹—[tetrafluorobenzofuran, R² on ring]

| Example | R¹ | R² | mp (°C.) | | Elemental Analysis C | H |
|---------|----|----|----------|--|----|---|
| 6 | H | 7-Cl | oil | Found | 39.97 | 1.30 |
| | | | | Calc'd | 42.41 | 1.33 |
| 7 | H | 5-Br | oil | Found | 41.57 | 1.64 |
| 8 | H | 5-CH₃ | oil | Calc'd | 52.44 | 2.93 |
| | | | | Found | 47.62 | 2.65 |
| 9 | H | 5-CH₂—CO₂CH₃ | oil | | | |
| 10 | 5-NO₂ | 7-Cl | 47–48.5 | Calc'd | 35.38 | 0.74 |
| | | | | Found | 35.27 | 0.77 |
| 11 | [phthalimido group, 5-N] | 7-Cl | 135.5–137 | Calc'd | 51.71 | 1.63 |
| | | | | Found | 52.30 | 1.70 |
| 12 | 5-NH₂ | 7-Cl | oil | | | |
| 13 | 5-NH₂ | H | oil | Calc'd | 46.39 | 2.43 |
| | | | | Found | 46.47 | 2.37 |
| 14 | H | 5-CN | 99–100 | Calc'd | 49.79 | 1.39 |
| | | | | Found | 49.87 | 1.27 |
| 15 | 6-NH₂ | H | oil | | | |
| 16 | 7-NH₂ | H | oil | | | |

Example 17 illustrates synthesis of a typical pyrazoline insecticide from a tetrafluorobenzofuran of the invention, such as may be produced from the product of Example 1.

EXAMPLE 17

Preparation of N-(2,2,3,3-tetrafluorobenzofuran-5-yl)-3-(4-difluoromethoxyphenyl)-4-phenylpyrazoline-1-carboxamide (A) Hydrogenation of 2.15 g (0.011 mole) of 5-nitro-2,2,3,3-tetrafluorobenzofuran (prepared as in Example 1, Part A) with a catalytic amount (0.25 g) of platinum oxide in 150 ml of methanol produced 2.15 g of 5-amino-2,2,3,3-tetrafluorobenzofuran.

(B) A solution of 0.75 g (0.0036 mole) of the 5-amino-2,2,3,3-tetrafluorobenzofuran of part A, dissolved in 109 ml of toluene, was added dropwise to a stirred solution of 8.0 ml 20% phosgene in toluene. After complete addition the mixture was heated at reflux for two hours. The mixture was cooled and the solvent removed by evaporation under reduced pressure leaving a residue. This residue was dissolved in 15 ml of diethyl ether and added to a stirred solution of 1.04 g (0.0036 mole) 3-(4-di-fluoromethoxyphenyl)-4-phenylpyrazoline and three drops of tri-ethylamine in 100 ml of diethyl ether. After complete addition the mixture was heated at reflux for one hour, then cooled to room temperature and stirred for approximately 18 hours. The solvent was removed from the reaction mixture by evaporation under reduced pressure leaving a solid residue. Recrystallization from ethanol provided 0.99 g of N-(2,2,3,3-tetrafluorobenzofuran-5-yl)-3-(4-difluoromethoxyphenyl)-4-phenylpyrazoline-1-carboxamide (mp 155°–159° C.). The nmr spectrum and elemental analysis were consistent with the proposed structure.

What is claimed is:

1. A cyclization process for preparing benzofurans of the formula:

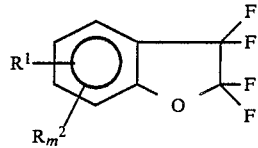

which comprises contacting, at elevated temperature in an aprotic solvent, an ether of the formula:

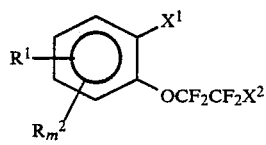

with a catalyst comprising a mixture of metallic copper and a ligand therefor, and separating the resulting benzofuran, wherein R¹ is hydrogen, nitro, amino, phthalimido or acetamido, R² is hydrogen or a substituent which is non-interfering in the cyclization, m is 0–3, and X¹ and X² independently are chloro, bromo or iodo.

2. The process of claim 1 wherein R² is at least one of hydrogen, halo, cyano, alkyl, hydroxy, alkoxy, acyl, acyloxy, alkoxycarbonyl, alkoxycarbonylalkyl, phenyl, phenyloxy, trifluoromethyl or dialkylamino.

3. The process of claim 1 wherein the ligand is 2,2'-dipyridyl, 1,10-phenanthroline or a substituted derivative thereof.

4. The process of claim 1 wherein the metallic copper is activated copper.

5. The process of claim 1 wherein the solvent is dimethyl sulfoxide, dimethylacetamide, dimethylformamide, hexamethylphosphorous triamide, N-methylpyrrolidone or sulfolane.

6. The process of claim 1 wherein $R^2$ is chloro, m is 1, $R^1$ is nitro, $X^1$ is chloro, and $X^2$ is bromo.

7. The process of claim 1 wherein m is 0, $R^1$ is nitro, $X^1$ is chloro and $X^2$ is bromo.

8. The process of claim 1 wherein the temperature is about 100°–150° C., the solvent is dimethyl sulfoxide, the ligand is 2,2'-dipyridyl, $R^1$ is nitro, $R^2$ and $X^1$ are chloro, m is 1, and $X^2$ is bromo.

9. The process of claim 1 wherein the temperature is in the range of about 110°–140° C., the solvent is dimethyl sulfoxide, the ligand is 2,2'-dipyridyl, $R^1$ is nitro, m is 0, $X^1$ is chloro, and $X^2$ is bromo.

10. The process of claim 1 wherein $R^1$ is hydrogen, $R^2$ is chloro, m is 1, $X^1$ is chloro and $X^2$ is bromo.

11. The process of claim 1 wherein $R^1$ is hydrogen, $R^2$ is methyl, m is 1, $X^1$ is chloro and $X^2$ is bromo.

* * * * *